(12) United States Patent
Kim et al.

(10) Patent No.: US 8,071,944 B2
(45) Date of Patent: Dec. 6, 2011

(54) PORTABLE ELECTRON MICROSCOPE USING MICRO-COLUMN

(75) Inventors: Ho Seob Kim, Chonan-si (KR); Byeng Jin Kim, Incheon (KR)

(73) Assignee: Cebt Co. Ltd. (KR)

( * ) Notice: Subject to any disclaimer, the term of this patent is extended or adjusted under 35 U.S.C. 154(b) by 176 days.

(21) Appl. No.: 11/792,156

(22) PCT Filed: Sep. 1, 2005

(86) PCT No.: PCT/KR2005/002903
§ 371 (c)(1),
(2), (4) Date: Jun. 1, 2007

(87) PCT Pub. No.: WO2006/025705
PCT Pub. Date: Mar. 9, 2006

(65) Prior Publication Data
US 2008/0315096 A1 Dec. 25, 2008

(30) Foreign Application Priority Data
Sep. 1, 2004 (KR) .................. 10-2004-0069731

(51) Int. Cl.
*G01N 23/00* (2006.01)
(52) U.S. Cl. ........ 250/311; 250/306; 250/307; 250/310; 250/492.1; 250/492.3

(58) Field of Classification Search .................. 250/311, 250/306, 307, 310, 441.11, 492.1, 492.2, 250/492.21, 492.3
See application file for complete search history.

(56) References Cited

U.S. PATENT DOCUMENTS

| | | | | |
|---|---|---|---|---|
| 4,663,559 A | * | 5/1987 | Christensen | 313/336 |
| 5,248,636 A | * | 9/1993 | Davis et al. | 438/709 |
| 5,412,180 A | * | 5/1995 | Coombs, III | 219/385 |
| 6,023,060 A | * | 2/2000 | Chang et al. | 850/9 |
| 6,369,385 B1 | * | 4/2002 | Muray et al. | 850/9 |
| 6,451,120 B1 | * | 9/2002 | Hubbard et al. | 118/719 |
| 7,329,878 B2 | * | 2/2008 | Kim | 250/396 R |
| 2003/0010911 A1 | * | 1/2003 | Palmer et al. | 250/306 |
| 2004/0144922 A1 | * | 7/2004 | Hayashibara et al. | 250/310 |
| 2004/0207424 A1 | * | 10/2004 | Hollman | 324/758 |
| 2004/0262541 A1 | * | 12/2004 | Honda et al. | 250/492.2 |
| 2005/0178966 A1 | * | 8/2005 | Gross | 250/311 |
| 2006/0193037 A1 | * | 8/2006 | Strait | 359/391 |

* cited by examiner

*Primary Examiner* — Robert Kim
*Assistant Examiner* — Michael Logie
(74) *Attorney, Agent, or Firm* — John K. Park; Park Law Firm

(57) ABSTRACT

Provided is a portable electron microscope using a microcolumn. The portable electron microscope includes a microcolumn, a low vacuum pump, a high vacuum pump, an ultra-high vacuum ion pump, a first chamber for receiving and fixing the microcolumn and a sample to be measured and forming a vacuum by means of the pumps, a controller, and a case for receiving the pumps, the chamber and the controller.

19 Claims, 4 Drawing Sheets

[Fig. 1]
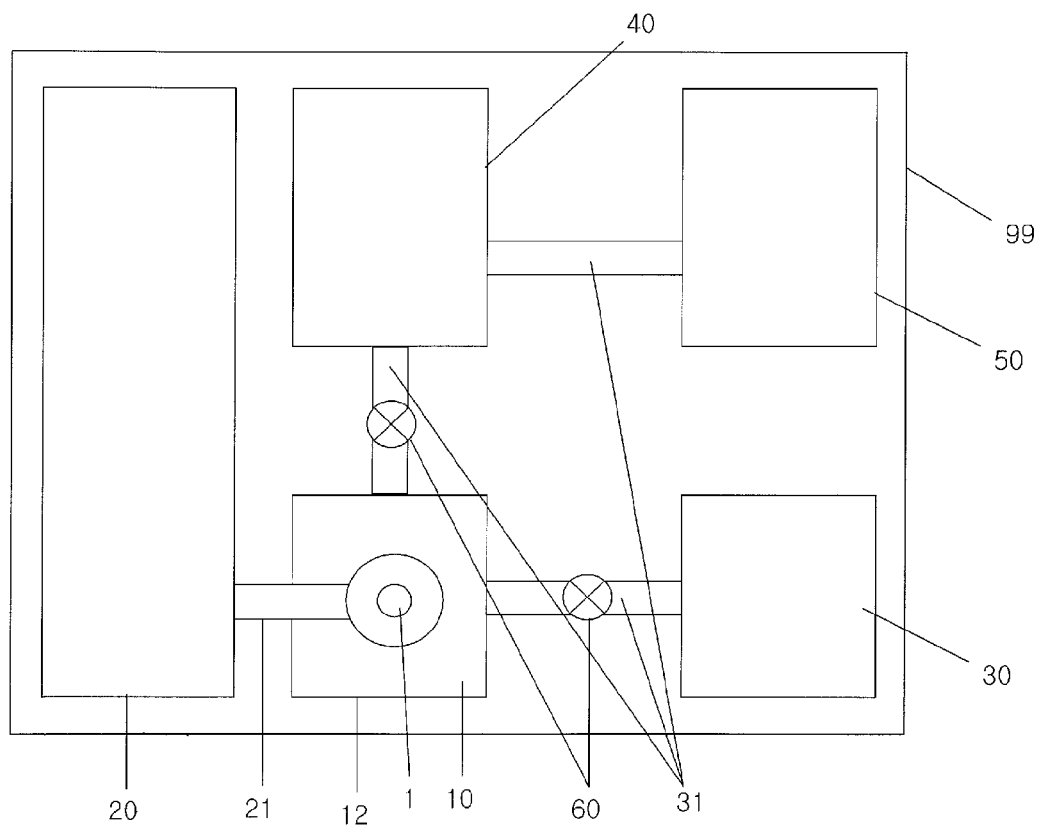
[Fig. 2]
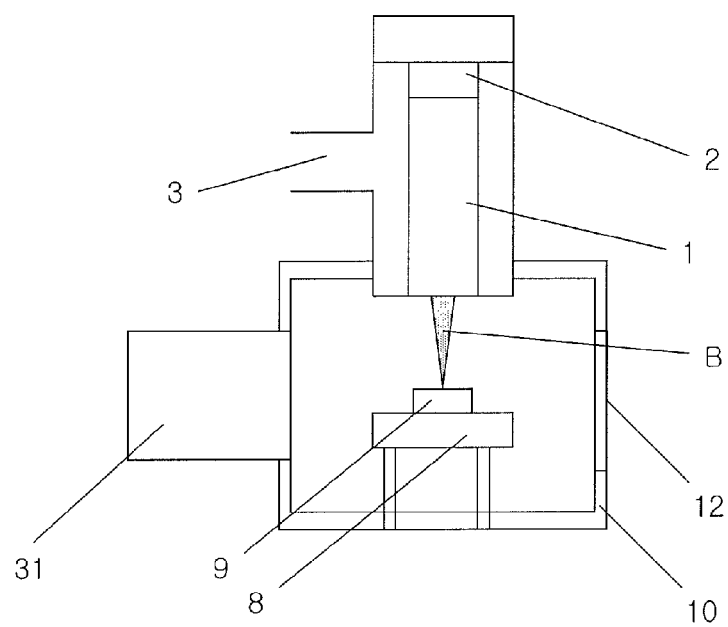

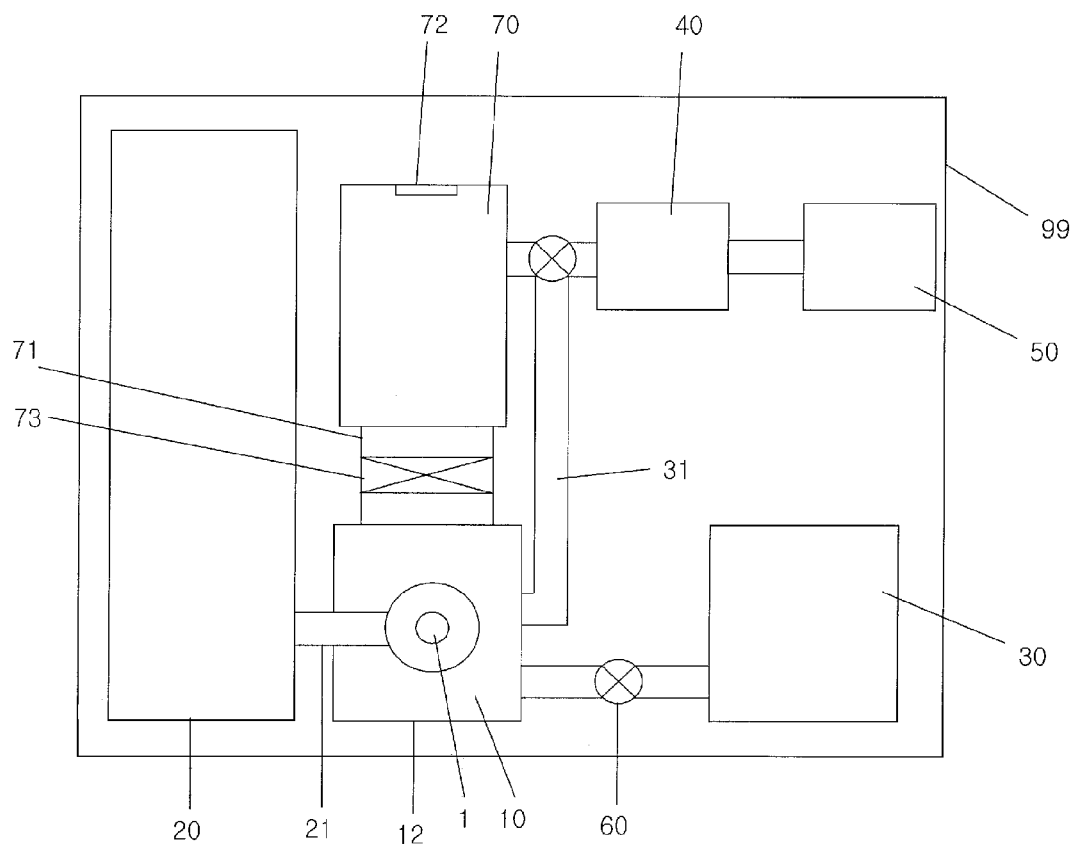
[Fig. 3]

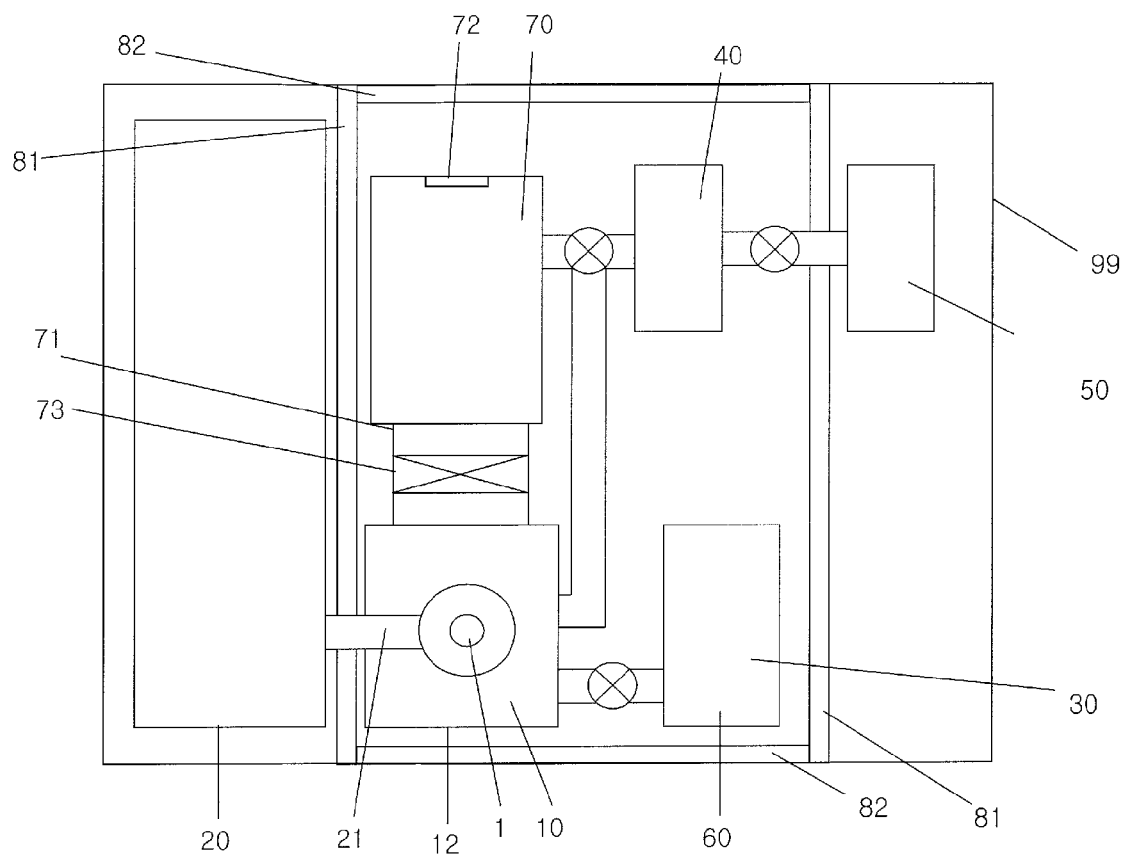
[Fig. 4]

[Fig. 5]
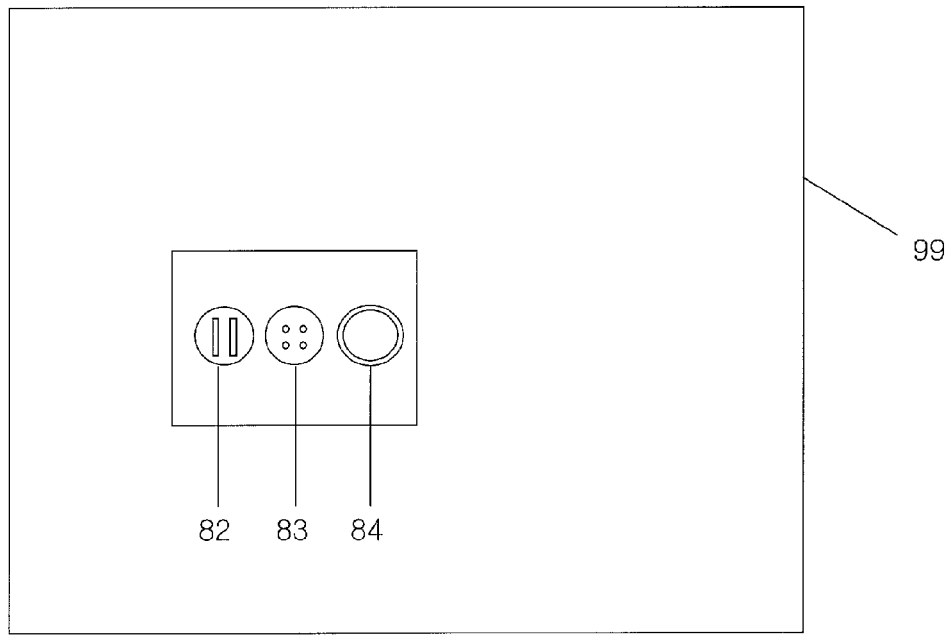
[Fig. 6]
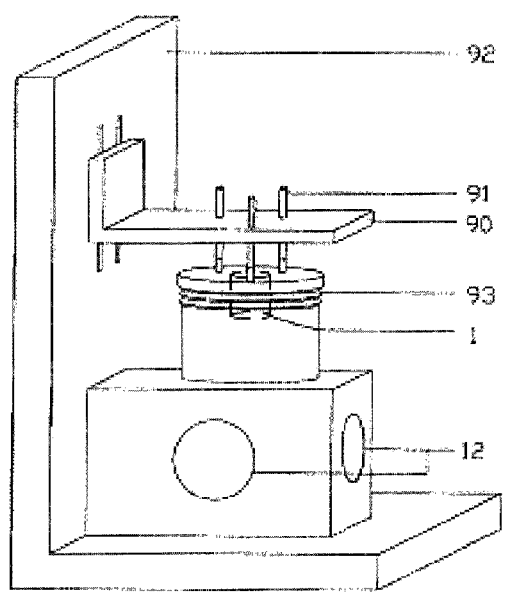

PORTABLE ELECTRON MICROSCOPE USING MICRO-COLUMN

TECHNICAL FIELD

The present invention relates to a portable electron microscope, and more particularly to a portable electron microscope employing a microcolumn to be easily carried and conveniently used.

BACKGROUND ART

A microcolumn has been initially introduced in the 1980s as an electron beam microcolumn based on an electron emitter and an electronic optical element of a microstructure which operate under the basic principle of a scanning tunneling microscope (STM). The electron beam microcolumn forms an improved column by delicately assembling fine elements to minimize an optical numerical value.

The microcolumn generally includes an electron emitter, a source lens, an Einzel lens, and a deflector. With regard to the microcolumn, the structure of a single microcolumn is disclosed in Korean Patent Application No. 2003-66003 as an example. Related papers include "An electron beam microcolumn with improved resolution, beam current, and stability" by E. Kratschmer et al. 6, J. Vac. Sci. Technol. B13(6), pp. 2498-2503, 1995, and "Experimental evaluation of a 20×20 mm footprint microcolumn" J. Vac. Sci. Technol. B14(6), pp. 3792-3796, 1996. Related patents include U.S. Pat. Nos. 6,297,584, 6,281,508, and 6,195,214. A multi-microcolumn may be composed of a single column module (SCM) where a plurality of single microcolumns are arranged in series or parallel, or two or more standardized monolithic column modules (MCMs), i.e, a multi-column adopting 2×1 or 2×2 as a set. Further, there is a multi-column structure composed of a wafer-scale column module (WCM) where a piece of wafer acts as a lens element of a column. This basic concept is disclosed in a paper "Electron beam microcolumns for lithography and related applications" by T. H. P. Chang et al. 8, J. Vac. Sci. Technol. B14, pp. 3774-3781, 1996. Another mode is a hybrid multi mode in which one or more columns may be arranged together with SCM and MCM or WCM, and some lens elements of the column may employ SCM, MCM, or WCM. Basic experimental results of this are disclosed in papers "Multi-beam microcolumns based on arrayed SCM and WCM" by Ho-Seob KIM et al. 7 persons, Journal of the Korean Physical Society, Vol. 45, No. 5, pp. 1214-1217, 2004, Microelectronic Engineering by Ho-Seob KIM et al. 6, pp. 78-79, pp. 55-61, 2005, and "Arrayed microcolumn operation with a wafer-scale Einzel Lens".

The conventional electron microscope is very large in size. Thus, when being observed by the electron microscope, a sample should be carried to a place such as a research institute where the electron microscope exists. This is inconvenient in the temporal and spatial aspect.

DISCLOSURE OF INVENTION

Technical Problem

It is an objective of the present invention to provide a portable or movable electron microscope using a microcolumn.

It is another objective of the present invention to provide a microscope capable of moving without temporal-spatial restriction to observe a sample.

Technical Solution

A portable electron microscope according to the present invention comprises:

a microcolumn;

a low vacuum pump;

a high vacuum pump;

an ultra-high vacuum pump;

a first chamber for receiving and fixing the microcolumn and a sample to be measured, and forming a vacuum by means of the pumps;

a controller; and a case for receiving the pumps, the chamber and the controller.

In general, the electron microscope is adapted to allow an electron beam to be irradiated onto a sample in a vacuum state and then check the reflected electron beam to observe the sample. Therefore, the microcolumn includes an electron emitter, a source lens, a deflector, and a focusing lens, and emits the electron beam in the vacuum state.

The portable electron microscope of the present invention produces an ultra high vacuum to place the sample and microcolumn in the vacuum state, which includes a mechanical or rotary pump, a turbo pump 40 for producing a high vacuum, and an ion or getter pump for producing an ultra-high vacuum. The low vacuum has the range of atmospheric pressure to $10^{-3}$ torr. The high vacuum has the range of about $10^{-3}$ to $10^{-7}$ torr. And the ultra-high vacuum has the range of about $10^{-7}$ to $10^{-11}$ torr. The chamber used in the present invention is preferably a cubic type chamber of about 2.75 inches.

The microcolumn is mounted in the chamber, and includes a micro electron lens provided with an aperture that has a diameter of several to several hundreds of micrometers and is delicately machined by semiconductor or MEMS (Micro-Electro-Mechanical Systems) processes. Further, the microcolumn has a total length of 10 mm or less from an electron emitting portion of the electron emitter to a final electrode of a final electron lens. However, the total length may be longer than this value if necessary. The microcolumn may have various shapes such as a cylinder having a diameter of about 20 mm and a length of about 22 mm, a hexahedron having a size similar to the cylinder, etc. However, the whole size of the microcolumn may vary according to the sizes of the electron emitter, lenses and deflector which are used in the microcolumn. Therefore, the smaller microcolumn may be used.

The portable electron microscope using the microcolumn can be manufactured to have a size of 400 mm×500 mm×400 mm. The microcolumn should be used in a vacuum chamber. To this end, the microcolumn is generally mounted in a cubic chamber of about 2.75 inches. As the vacuum chamber, a fitting flange such as a 6 or 4 way cross may be used. The size or shape of the chamber may be determined according to the sample to be measured. If the sample to be measured is large or requires to use a stage, the chamber preferably has a large size. When only a small sample is measured, the chamber may have a small size. In this case, the stage on which the sample can move becomes small, and thus a traveling distance of the stage becomes short. Therefore, the size of the portable electron microscope may be additionally determined according to the size of the chamber in which the microcolumn is mounted and the size of the pump. It is natural that the portable electron microscope can be manufactured at a little larger size in consideration of a capacity of the pump etc.

Advantageous Effects

With the portable electron microscope according to the present invention, it is possible to simply and easily observe the sample at a desired place without temporal-spatial restriction.

BRIEF DESCRIPTION OF THE DRAWINGS

FIG. 1 is a top view showing an embodiment of a portable electron microscope of the present invention.

FIG. 2 is a cross-sectional view showing a layout of a microcolumn and a chamber in accordance with the present invention.

FIG. 3 is a top view showing another embodiment of a portable electron microscope of the present invention.

FIG. 4 is a top view showing yet another embodiment of a portable electron microscope of the present invention.

FIG. 5 is a side view showing the outside of a case of a portable electron microscope of the present invention.

FIG. 6 is a schematic perspective view showing an example of movement, for example tilting, of a microcolumn used in the present invention.

BEST MODE FOR CARRYING OUT THE INVENTION

Hereinafter, a portable electron microscope of the present invention will be described in detail with reference to the attached drawings.

FIG. 1 is a top view schematically showing the basic structure of a portable electron microscope according to the present invention. The portable electron microscope is housed in a case 99 in which a controller 20, a chamber 10, an ultra-high vacuum pump 30 such as an ion pump and/or a getter pump, a high vacuum pump 40 such as a turbo pump on the chamber, and a low vacuum pump 50 such as a mechanical pump on the right side of the high vacuum pump 40 are located. A computer (not shown) such as a notebook may be connected to the controller 20 in order to conveniently control the controller 20. Of course, the layout of FIG. 1 is not necessarily fixed, but may be varied according to sizes of the case and other elements.

The controller 20 is connected to the chamber 10 through a control line 21 to control the electron beam of a microcolumn 1 and to observe a sample, and may have a wiring (not shown) to control the various pumps. The chamber 10 receives and fixes the microcolumn 1 and is provided with a loader (not shown) to place the sample therein and a door 12 capable of inserting the sample. Further, the chamber 10 is connected to the pumps through vacuum lines 31. As shown, for the sake of spatial efficiency, the high vacuum pump 40 and the low vacuum pump 50 are preferably connected to the chamber 10 by a valve 60. As to operational sequence, first, the sample is fixed to the loader of the chamber through the door 12. The valve 60 for the low vacuum pump 50 such as the mechanical pump and the high vacuum pump 40 such as the turbo pump is opened to make the inside of the chamber in a high vacuum state. Then, the ultra-high vacuum pump 30 such as the ion pump makes the inside of the chamber 10 in an ultra-high vacuum state. When the inside of the chamber 10 becomes the ultra-high vacuum state, the controller 20 actuates the microcolumn 1. Thereby, it is possible to observe the sample.

When being maintained in a constant vacuum state, the chamber is closed by valves. However, the valve connected to the ion pump continues to be opened while the vacuum state is maintained. It does not matter that the two valves other than the valve between the chamber and the turbo pump are not provided in order to decrease volume and weight of the equipment.

FIG. 2 is a cross-sectional view showing a layout of a microcolumn 1 and a chamber 10 in accordance with the present invention. In general, the microcolumn 1 is mounted to a feedthrough 2 and fixed to one port of the vacuum chamber 10. The inside of the vacuum chamber 10 is installed with a loader 8 or stage capable of fixing a sample 9 to be measured. The fixed sample 9 is measured by an electron beam B emitted from the microcolumn 1 in an equal or similar way to the principle measured at a general electron microscope. At this time, the microcolumn should maintain an ultra-high vacuum, and preferably a degree of vacuum of $10^{-9}$ torr or more. However, the inside of the chamber in which the sample is located does not need to maintain the ultra-high vacuum, and can maintain a degree of vacuum corresponding to a high vacuum by means of a high vacuum pump through a vacuum line 31. Thus, the chamber 10 can maintain a degree of vacuum different from the microcolumn 1. In other words, the degree of vacuum can be made differential. To this end, all except an aperture of a lens of the microcolumn are sealed, and the ultra-high vacuum pump is connected to the microcolumn 1 and the feedthrough 2 rather than the chamber 10 using a T-type or cross flange 3 or a separate chamber. If the differential type is not used, the flange 3 may be not used.

MODE FOR THE INVENTION

FIG. 3 is a top view showing another embodiment of a portable electron microscope according to the present invention. In this embodiment, a chamber 70 capable of separately loading only a sample is further provided compared to the embodiment of FIG. 1. The measuring chamber 10 and the loading chamber 70 can be connected by a loading passage 71. A door 72 is provided in the passage 71 to open on carrying the sample and to close on observing the sample. Since it takes much time to make the inside of the chamber 10 in an ultra-high vacuum state, the inside of the chamber 10 is made near to the ultra-high vacuum state in advance, and only the sample is loaded in the separate chamber 70, and carried into the measuring chamber 10 through the loading passage 71 using a linear carrier. In this embodiment, the chamber 10 is made in the ultra-high vacuum state by valves 60 and 73 in advance. The sample is inserted into the chamber 70, and the chamber 70 is made in a high vacuum state using a mechanical pump 50 and a turbo pump 40. Then, the sample is carried into the measuring chamber 10 so as to be measured by the microcolumn 1 through the loading passage 71. It does not matter that a vacuum tube or line 31 directly connecting the turbo pump 40 and the chamber 10 is eliminated because it is used to accelerate the vacuum in the chamber. However, when a stage exists in the chamber, a stage portion and a microcolumn portion are divided by a valve (not shown), and the vacuum line 31 is used to maintain the vacuum of the stage portion when the sample is inserted or discharged.

FIG. 4 is a top view showing an embodiment of mounting thermoelements or heating devices 81 and 82 to the portable electron microscope of FIG. 3. This embodiment is for easily making an ultra-high vacuum. To this end, chambers 10 and 70 are baked at a temperature of about 100° C. In contrast, a controller 20 which is a precise electronic element is vulnerable to heat and so partitioned by the thermoelement 81.

Thereby, the chamber 10 is adapted to be baked, and the controller 20 is adapted to be operated in a low temperature state. Thus, the controller 20 and the mechanical pump 50 are located outside so as to maintain a low temperature by means of the thermoelements 81 and 82 or a heating tape, and the chambers 10 and 70, the turbo pump 30 and the ion pump 40 are located inside so as to maintain a high temperature. As shown in the embodiment of FIG. 3, all the portable electron microscopes can be realized on the principle as described above.

FIG. 5 is a side view showing the outside of a case 99 of a portable electron microscope according to the present invention. The outside of the case 99 is provided with a power terminal 82, a control terminal 83 capable of being connected to a notebook etc., and an air connector 84 for discharge and intake of air or gas. The air connector 84 is used when being connected to a chamber and/or a pump to vent a vacuum. The portable electron microscope of the present invention has an advantage in that the vacuum can be maintained by battery power of an automobile while carrying because the microcolumn has a small size and the chamber has also a small size.

FIG. 6 is a perspective view schematically showing the structure capable of tilting and/or vertically moving a microcolumn 1 in the various embodiments of the portable electron microscope of the present invention as described above.

A chamber 10 is supported by a support 92 fixed to a case 99, and the microcolumn 1 is fixed to a fixture 93 of a bellows type. A top surface of the fixture 93 is tilted by three positioners 91. The positioners 91 and the fixture 93 are all supported by a slider 90 to enable vertical movement. The positioners 91 rotate at the slider 90, and are fixed to the fixture 93, for example, by screws to adjust a relative distance between the slider 90 and the fixture 93. FIG. 6 illustrates only one of the vertical movement and/or the tilting of the microcolumn 1. This method may be variously performed by those skilled in the art. In the present invention, this function allows the sample to be observed by causing the microcolumn to move up, down, left and right or to be tilted at an arbitrary angle, which is different from the convention function where the electron microscope observes the sample in a fixed state without movement.

In the above-mention configuration of the present invention, the microcolumn can be used in a single or multiple type. The multi-microcolumn may be used by combining a plurality of single microcolumns or in various types, such as a wafer type etc., manufactured in a semiconductor process.

INDUSTRIAL APPLICABILITY

The portable electron microscope using the microcolumn according to the present invention can be used for portable inspection equipment or lithography.

The invention claimed is:

1. A portable electron microscope, comprising:
a microcolumn;
a low vacuum pump for producing a low vacuum of range of atmospherical pressure to about $10^{-3}$ torr;
a high vacuum pump for producing a high vacuum of range of about $10^{-3}$ torr to about $10^{-7}$ torr;
an ultra-high vacuum pump for producing an ultra-high vacuum of range of about $10^{-3}$ torr to about $10^{-11}$ torr;
a chamber for receiving and fixing the microcolumn and a sample to be measured, and forming a vacuum by means of the pumps;
a controller; and
a case for receiving pumps, the chamber and the controller,
wherein the portable electron microscope has a size smaller than 400 mm×500 mm×400 mm to be movable, and
wherein the case is partitioned into a high-temperature partition and a low-temperature partition and the chamber is disposed in the high-temperature partition of the case and the controller is disposed in the low-temperature partition of the case such that the chamber and the controller are isolated and blocked thermally from each other, such that the controller is protected from the bake-out heat of the chamber for bake-out of the chamber in the high-temperature partition of the case, and such that the controller is maintained in a low temperature and the chamber is maintained in a high temperature.

2. The portable electron microscope according to claim 1, wherein the microcolumn moves relatively to the sample to be measured, and performs one of tilting and vertical movement.

3. The portable electron microscope according to claim 2, further comprising a loader on which the sample is placed, a carrying means for carrying the loader to a first chamber, and a second chamber for receiving the loader and connected in a vacuum state by the first chamber and an open-close door so that the carrying means moves to the first chamber, wherein the sample is placed on the loader and carried to the first chamber by the carrying means.

4. The portable electron microscope according to claim 3, further comprising a thermoelement, a heating tape, or a thermoelement and a heating tape between the high-temperature partition and the low-temperature partition of the case, wherein the bake-out is performed by the thermoelement, the heating tape, or the thermoelement and the heating tape equipped in the case.

5. The portable electron microscope according to claim 4, wherein a degree of vacuum becomes differential such that the microcolumn maintains an ultra-high vacuum and the chamber maintain a low vacuum or high vacuum.

6. The portable electron microscope according to claim 3, wherein the microcolumn is used as a multi-microcolumn.

7. The portable electron microscope according to claim 2, wherein a degree of vacuum becomes differential such that the microcolumn maintains an ultra-high vacuum and the chamber maintain a low vacuum or high vacuum.

8. The portable electron microscope according to claim 2, wherein the microcolumn is used as a multi-microcolumn.

9. The portable electron microscope according to claim 1, further comprising a loader on which the sample is placed, a carrying means for carrying the loader to a first chamber, and a second chamber for receiving the loader and connected in a vacuum state by the first chamber and an open-close door so that the carrying means moves to the first chamber, wherein the sample is placed on the loader and carried to the first chamber by the carrying means.

10. The portable electron microscope according to claim 9, wherein the bake-out is performed by any one of a thermoelement and a heating tape and received in the case.

11. The portable electron microscope according to claim 10, wherein a degree of vacuum becomes differential such that the microcolumn maintains an ultra-high vacuum and the chamber maintain a low vacuum or high vacuum.

12. The portable electron microscope according to claim 9, wherein the microcolumn is used as a multi-microcolumn.

13. The portable electron microscope according to claim 1, further comprising a thermoelement, a heating tape, or a thermoelement and a heating tape between the high-temperature partition and the low-temperature partition of the case for keeping the bake-out heat of the chamber in the high-temperature partition off the controller in the low-temperature partition, wherein the bake-out is performed in the chamber enclosed by the thermoelement, the heating tape, or the thermoelement and the heating tape equipped in the case.

14. The portable electron microscope according to claim 13, wherein a degree of vacuum becomes differential such that the microcolumn maintains an ultra-high vacuum and the chamber maintain a low vacuum or high vacuum.

15. The portable electron microscope according to claim 13, wherein the microcolumn is used as a multi-microcolumn.

16. The portable electron microscope according to claim 1, wherein a degree of vacuum becomes differential such that the microcolumn maintains an ultra-high vacuum and the chamber maintain a low vacuum or high vacuum.

17. The portable electron microscope according to claim 16, wherein the microcolumn is used as a multi-microcolumn.

18. The portable electron microscope according to claim 1, wherein the microcolumn is used as a multi-microcolumn.

19. The portable electron microscope according to claim 1, wherein a degree of vacuum becomes differential such that the microcolumn maintains an ultra-high vacuum and the chamber maintain a low vacuum or high vacuum.

* * * * *